United States Patent [19]

Drent

[11] Patent Number: 4,876,401
[45] Date of Patent: Oct. 24, 1989

[54] PROCESS FOR THE PREPARATION OF ALKANEDIOLS

[75] Inventor: Eit Drent, Amsterdam, Netherlands

[73] Assignee: Shell Oil Company, Houston, Tex.

[21] Appl. No.: 321,247

[22] Filed: Mar. 9, 1989

[30] Foreign Application Priority Data

Mar. 18, 1988 [GB] United Kingdom ............ 8806526

[51] Int. Cl.$^4$ .................. C07C 29/17; C07C 31/20
[52] U.S. Cl. ...................... 568/861; 568/851
[58] Field of Search .................................. 568/861

[56] References Cited

U.S. PATENT DOCUMENTS

| | | | |
|---|---|---|---|
| 2,950,326 | 8/1960 | Hort | 568/861 |
| 2,953,605 | 9/1960 | Hort | 568/861 |
| 2,967,893 | 1/1961 | Hort et al. | 568/861 |
| 2,992,278 | 7/1961 | Tedeschi | 568/861 |
| 4,011,277 | 3/1977 | Nishida et al. | 568/861 |
| 4,213,000 | 7/1980 | Costes | 568/861 |
| 4,268,454 | 5/1981 | Pez et al. | 568/861 |
| 4,438,285 | 3/1984 | Codignola | 568/861 |
| 4,599,466 | 7/1986 | Mueller et al. | 568/861 |

*Primary Examiner*—J. E. Evans

[57] ABSTRACT

A process for the preparation of alkanediols, which comprises reacting: (a) a monoalkynically and/or a monoalkenically unsaturated diol, wherein the alcohol groups are separated by at least two carbon atoms, which carbon atoms form the alkynic and/or alkenic unsaturated entity respectively, and (b) hydrogen, in the presence of a palladium compound and a base.

21 Claims, No Drawings

PROCESS FOR THE PREPARATION OF ALKANEDIOLS

FIELD OF THE INVENTION

The invention relates to a process for the preparation of alkanediols, having at least two carbon atoms separating the alcohol groups. More particular, the process relates to the preparation of said alkanediols via a catalytic hydrogenation of the corresponding alkyne- or alkenediols.

BACKGROUND OF THE INVENTION

Alkanediols such as butane-1,4-diol, are the focus of a lot of attention in view of their high potential for the chemical industry, especially in the preparation of polyurethane foams and polymers, in polyesters as well as for the preparation of tetrahydrofuran. In spite of a still growing demand for these alkanediols the use of these alkanediols is still rather restricted due to the problems encountered in their preparation, which generally proceeds via the catalytic hydrogenation of the corresponding alkynediol. With the preparation of e.g. butane-1,4-diol, it is known that the catalytic hydrogenation of but-2-yne-1,4-diol to butane-1,4-diol proceeds via the formation of the intermediate but-2-ene-1,4-diol, which compound is however known to isomerize to γ-hydroxy-butyraldehyde thereby decreasing the yield of the desired alkanediols. Although it is possible in principle to hydrogenate γ-hydroxy-butyraldehyde to butane-1,4-diol, said hydrogenation is considerably more difficult than the hydrogenation of the olefinically unsaturated double bonds. A further problem relates to the preparation of the alkanediol, as described hereinbefore is, that the catalysts which are effective in the hyrogenation of the unsaturated groups, e.g. noble metals and especially palldium (Pd), are frequently also effective isomerization catalyst, i.e. they promote the formation of compounds such as γ-hydroxy-butyraldehyde.

In U.S. Pat. No. 4,438,285, a process is described for the catalytic hydrogenation of but-2-yne-1,4-diol to butane-1,4-diol, which process is conducted at a temperature from 60°–180° C., preferably at a temperature of 110° C., wherein the catalyst comprises ruthenium and palladium in a 4:1 molar ratio, the ruthenium being present in order to catalyze the hydrogenation of any γ-hydroxy-butyraldehyde formed. This process has a disadvantage in that it employs a very expensive catalyst.

Hence it can be concluded that there is need for further improvement in the preparation of alkanediols via a catalytic hydrogenation of the corresponding alkyne- and/or alkenediols.

The problem underlying the present invention is finding a process for the preparation of alkanediols, which does not suffer from one or more of the problems hereinbefore described.

As a result of continuing and extensive research and experimentation, it has been found that it is possible to prepare alkanediols of the before mentioned type, via a catalytic hydrogenation process which can be conducted under mild reaction conditions and employing a less expensive, single noble metal-based catalyst system, i.e. a palladium-based catalyst system.

SUMMARY OF THE INVENTION

The invention provides a process for the preparation of alkanediols, which comprises reacting: (a) monoalkynically and/or a monoalkenically unsaturated diol, wherein the alcohol groups are separated by at least two carbon atoms, which carbon atoms form the alkynic and/or alkenic unsaturated entity respectively, and (b) hydrogen in the presence of a palladium compound and a base.

DESCRIPTION OF THE PREFERRED EMBODIMENTS

The preparation of alkanediols via the process of the present invention may conveniently be carried out in the presence of a solvent or diluent; preferably the solvent or diluent is a polar organic compound, thereby providing a polar reaction medium.

The nature of the polar reaction medium is not critical and may comprise one or more liquid polar organic compounds, as well as mixtures thereof with water. It will be appreciated by persons skilled in the art that it would be advantageous to use a polar reaction medium which is inert with respect to the hydrogenation reaction, i.e. which does not interfere with the desired reaction. Suitable polar organic compounds include linear and cyclic mono- and polyethers such as ethylene glycol dimethyl ether, ethylene glycol diethyl ether, diethylene glycol dimethyl ether (diglyme), diethylene glycol diethyl ether, triethylene glycol dimethyl ether, tetrahydrofuran, dioxan, diphenylether, ethylene glycol monomethyl ether, ethylene glycol monoethyl ether, ethylene glycol monobutyl ether, diethylene glycol monomethyl ether, diethylene glycol monoethyl ether, diethylene glycol monopropyl ether, propylene glycol monomethyl ether, 1,3-propanediol monomethyl ether and the like. Alcohols, such as those in the preparation of the alkali or alkaline-earth metal alcoholates, as described hereinafter as well as the alkanediols prepared by the process of the present invention may also serve as a polar solvent. Diglyme is a preferred polar organic compound for use as polar reaction medium.

The nature of the palladium compounds, which may be employed in the process of the present invention, is not critical, provided they are at least partly soluble in the reaction medium. Suitable palladium compounds include those based on coordinating as well as on non-coordinating acids such as palladium carboxylates as exemplified by palladium formate and palladium acetate; palladium halogenates as exemplified by palladium chloride; palladium sulfate, palladium tosylate, palladium nitrate and the like. It will be appreciated that cation-providing palladium compounds are preferred.

The base which is employed in the process of the present invention together with the palladium compound, as described hereinbefore, may be an organic or an inorganic base.

Organic bases which may suitably be employed in the process of the present invention include alkali metal, alkaline-earth metal or ammonium alcoholates based on linear or branched aliphatic alcohols. Preferably such alcohols have 1–8 carbon atoms per molecule. Especially preferred are branched aliphatic alcohols such as tertiary alcohols, with tert-butyl alcohol and tert-amyl alcohol being preferred tertiary alcohols. Alkali metal alcoholates based on the tertiary alcohols as described hereinbefore, are preferred alcoholates; potassium tert-butylate and sodium tert-amylate being especially preferred.

It will be appreciated by one skilled in the art that when the process of the present invention is conducted in the presence of water and an alcoholate, as hereinbefore described, that as a result of the interaction of water and alcoholate, the corresponding hydroxide will be formed. Hence, when the preparation of the alkanediols is conducted in a water-containing reaction medium, the alcoholate may advantageously be replaced with an inorganic base. Inorganic bases which may be used in a water-containing reaction medium inclue alkali metal, alkaline-earth metal and ammonium hydroxides. Potassium hydroxide is a preferred alkali metal hydroxide.

The process of the present invention may conveniently be conducted at a temperature in the range of from about 15°–200° C. and a hydrogen pressure in the range of from atmospheric pressure to 100 bar. Preferably the process is conducted at a temperature in the range of from 25°–70° C. and a hydrogen pressure in the range of from 5–70 bar.

In the process of the present invention, the alkali metal, alkaline-earth metal or ammonium alcoholate may conveniently be introduced into the reactor as a ready-made compound or alternatively the alkali or alkaline-earth metal alcoholate may be prepared in situ in the polar reaction medium. According to the latter embodiment, the alkali or alkaline-earth metal alcoholate can conveniently be prepared by contacting an alkali or alkaline-earth metal or a hydride thereof, with a linear or branched aliphatic alcohol of the type as described hereinbefore, at elevated temperature, e.g. a temperature in the range at which the hydrogenation reaction is to be conducted i.e. 15°–100° C. According to this embodiment, the alcohol is preferably present in an amount which is at least stoichiometric with respect to the metal or hydride. Sodium hydride is a preferred alkali metal hydride in the process of the present invention.

When, in the process of the present invention the alkali or alkaline-earth metal alcoholate is prepared in situ, it is preferred to have a reaction medium which comprises hydroxyl group-free compounds and to delay the introduction of the unsaturated diols into the reaction, until substantially all the metal or hydride has been converted.

In the process of the present invention it is preferred that the base is employed in a molar excess over the palladium compound. Especially preferred is a process wherein the molar ratio of base to palladium compound is in the range of from 2:1 to 1000:1.

When an inorganic base, as described hereinbefore, is employed in the process of the present invention, said base may conveniently be added to the reaction medium as an aqueous solution.

The amount of palladium compound which may be used in the process of the present invention may vary over a wide range and will generally be in a range of from 0.001–1 mmol per g of alkynediol or alkenediol. Preferably the amount of palladium compound will be in the range of from 0.005–0.5 mmol per g of diol.

As mentioned hereinbefore, the starting compounds for the preparation of the alkanediols, via the process of the present invention, are monoalkynically or monoalkenically unsaturated diols, wherein the alcohol groups are separated by at least two carbon atoms. The present process is especially suited for the preparation of alkanediol wherein the alcohol groups are separated by only two carbon atoms. Preferred alkynically and alkenically unsaturated diols for the preparation of the alkanediols wherein the alcohol groups are separated by only two carbon atoms, are those of general formula

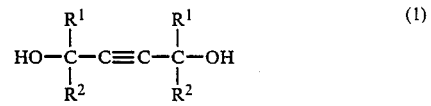

respectively of general formula

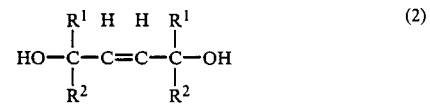

wherein each pair of $R^1$ and each pair of $R^2$ individually is H or $CH_3$.

The unsaturated diols to be used in the present process will generally be undiluted. However, it may sometimes be possible or even advantageous to employ such an unsaturated diol in diluted form, provided the diluent does not interfere with the process, i.e. the diluent is inert under the reaction conditions of the present process. An example of the use of a diluted unsaturated diol is the use of but-2-yne-1,4-diol as a starting material, which diol is available as an aqueous effluent from the reaction between aqueous formaldehyde and acetylene.

But-2-yne-1,4-diol is a preferred alkynically unsaturated diol for use as a starting material in the process of the present invention.

The unsaturated diol will generally be employed in such an amount that it comprises 5 to 75%m of the reaction medium, although higher and lower concentrations are not excluded.

Preferably the process is conducted at a temperature in the range of from 25°–70° C. and at a $H_2$ pressure in the range of from 5–70 bar.

The invention will be further described by the following examples which are illustrative and which are not intended to restrict the scope of the invention.

EXAMPLE I 1 mmol palladium acetate, 60 mmol sodium hydride, 120 mmol tert-amyl alcohol and 50 ml diglyme were introduced into a 250 ml stainless steel (Hastelloy C) autoclave, equipped with a magnetic stirrer and heated for 0.5 h at 45° C. This was followed by the addition of 20 ml tert-amyl alcohol, 50 ml diglyme and 10 g but-2-yne-1,4-diol and pressurizing the autoclave with $H_2$ until a $H_2$ pressure of 30 bar had been obtained. Subsequently the reactor contents were stirred at 45° C. for the time as indicated hereinafter. After cooling and depressurizing, the reactor contents were analyzed by gas liquid chromatography.

Process details and product analysis data are given in Table 1.

EXAMPLE II

The procedure as described in Example I was repeated employing the same compounds but in different amounts, while the reaction was conducted at a higher temperature.

EXAMPLE III

The procedure as described in Example I was again repeated with different amounts of the compounds and replacement of the addition of 20 ml tert-amyl alcohol and 50 ml diglyme after the alcoholate preparation, with 50 ml butane-1,4-diol. The hydrogenation was conducted at 50° C.

EXAMPLE IV 0.1 mmol palladium acette, 40 ml tert-amyl alcohol, 80 ml diglyme, 60 mmol potassium tert-butylate and 10 g but-2-yne-1,4-diol were introduced into a 250 ml stainless steel autoclave as described hereinbefore, which was followed by heating the reactor contents and pressurizing the autoclave with $H_2$ until a pressure of 60 bar had been obtained. Hereafter the procedure was the same as for Example I.

EXAMPLE V

This example is a repetition of Example IV, with the exception that only 1 mmol of potassium tert-butylate was employed and that the 20 ml tert-amyl alcohol was replaced with an equal volume of diglyme.

TABLE 1

| Example No. | | I | II | III | IV | V |
| --- | --- | --- | --- | --- | --- | --- |
| Pd. acetate | mmol | 1 | 1 | 0.1 | 0.1 | 0.1 |
| NaH | mmol | 60 | 10 | 10 | — | — |
| tert-amyl alcohol | mmol | 120 | 5 | 5 | — | — |
| diglyme | ml | 50 | 50 | 50 | — | — |
| heating | h at °C. | 0.5–45 | 0.5–45 | 0.5–45 | — | — |
| tert-amyl alcohol | ml | 20 | 20 | — | 40 | — |
| diglyme | ml | 50 | 50 | — | 80 | 100 |
| butane-1,4-diol | ml | — | — | 50 | — | — |
| K-tert-butylate | mmol | — | — | — | 60 | 1 |
| but-2-yne-1,4-diol | g | 10 | 10 | 10 | 10 | 10 |
| $P_{H2}$ | bar | 30 | 30 | 60 | 60 | 60 |
| heating | h* at °C. | 5–45 | 0.5–75 | 5–50 | 2–45 | 0.5–45 |
| but-2-yne-1,4-diol conversion | % m | 100 | 100 | 100 | 100 | 100 |
| butane-1,4-diol content of end product | % m | 86 | 95 | 90 | 95 | 94 |
| but-2-ene-1,4-diol content of end product | % m | 14 | 5 | 10 | 5 | 6 |

*The hydrogenation was stopped after the time indicated for sake of convenience, and hence the time should not be construed to be the end of catalyst activity.

Comparative Experiment A 10 mmol nickel formate, 60 mmol sodium hydride, 20 mmol tert-amyl alcohol and 50 ml diglyme were introduced into a 250 ml autoclave of the type as described hereinbefore, and heated for 0.5 h at 50° C. This was followed by the addition of 50 ml of diglyme, 30 ml tert-amyl alcohol and 10 g but-2-yne-1,4 diol and pressurizing the autoclave with $H_2$ until a pressure of 50 bar had been obtained. The reactor contents were heated for 2 h at 80° C. followed by 5 h at 100° C. Hereafter, the procedure was the same as for Example I.

Process details and product analysis data are given in Table 2.

Comparative Experiment B

In this experiment 2 of a palladium on carbon catalyst (5%m Pd), 100 ml diglyme and 10 g but-2-yne-1,4-diol were introduced into a 250 ml autoclave as described hereinbefore, which was followed by heating the reactor contents to 100° C. and pressurizing the autoclave with $H_2$ until a pressure of 30 bar had been obtained. Subsequently heating was continued for 2 h. Hereafter, the procedure was similar to that of experiment A.

Comparative Experiment C

This experiment was a repetition of Example IV with the exception that no potassium tert-butylate was used. The reaction was stopped after 0.5 h. Hereafter, the procedure was similar to that of experiment A.

TABLE 2

| Comparative Experiment No. | | A | B | C |
| --- | --- | --- | --- | --- |
| Pd acetate | mmol | — | — | 0.1 |
| Ni formate | mmol | 10 | — | — |
| NaH | mmol | 60 | — | — |
| Pd/C (5% m Pd) | g | — | 2 | — |
| tert-amyl alcohol | mmol | 20 | — | — |
| diglyme | ml | 50 | — | — |
| heating | h at °C. | 0.5–50 | — | — |
| tert-amyl alcohol | ml | 30 | — | 40 |
| diglyme | ml | 50 | 100 | 80 |
| but-2-yne-1,4-diol | g | 10 | 10 | 10 |
| $P_{H2}$ | bar | 50 | 30 | 60 |
| heating | h at °C. | 2–80 5–100 | 2–100 | 2–45 |
| but-2-yne-1,4 diol conversion | % m | 0 | trace | 100 |
| butane-1,4-diol content of end product | % m | — | — | 67 |
| but-2-ene-1,4-diol content of end product | % m | — | — | 33 |

From the results of Examples I–V it can be seen that by the process of the present invention butane 1,4-diol can be formed under mild conditions in high yield and with a high selectivity.

What is claimed is:

1. A process for the preparation of alkanediols which comprises the reacting: (a) a monoalkynically and/or monoalkenically unsaturated diol, wherein the alcohol groups are separated by at least two carbon atoms, which carbon atoms form the alkynic and/or alkenic unsaturated entity respectively, and (b) hydrogen, in the presence of a palladium compound which is at least partially soluble in the reaction medium and a base.

2. The process of claim 1 wherein said base is an organic base selected from an alkali metal alcoholate, an alkaline-earth metal alcoholate and an ammonium alcoholate based on a linear or branched aliphatic alcohol.

3. The process of claim 2 wherein said alkali or alkaline-earth metal alcoholate is formed in situ by reaction of an alkali or alkaline-earth metal or a hydride thereof and an aliphatic alcohol at a temperature in the range of from about 15° C. to about 100° C.

4. The process of claim 3 wherein said alcohol is present in an amount which is at least stoichiometric with respect to the metal or hydride.

5. The process of claim 3 wherein said alkali metal hydride is sodium hydride.

6. The process of claim 2 wherein said alcoholate is based on a $C_1$–$C_8$ alcohol.

7. The process of claim 2 wherein the branched aliphatic alcohol is a tertiary alcohol.

8. The process of claim 7 wherein the tertiary alcohol is selected from tert-butyl alcohol and tert-amyl alcohol.

9. The process of claim 1 wherein said base is an inorganic base selected from an alkali metal hydroxide, an alkaline-earth metal hydroxide and ammonium hydroxide.

10. The process of claim 9 wherein said base is employed in a molar excess over the palladium compound.

11. The process of claim 10 wherein a molar ratio of base to cationic palladium compound in the range of from about 2:1 to about 1000:1 is used.

12. The process of claim 1 wherein the palladium compound is used in an amount in the range of from about 0.001 to about 1 mmol per g of alkynediol or alkenediol.

13. The process of claim 12 wherein the palladium compound is used in an amount in the range of from 0.005–0.5 mmol per g of diol.

14. The process of claim 2 wherein the alkali metal alcoholate is selected from potassium tert-butylate and sodium tert-amylate.

15. The process of claim 1 wherein said process is conducted at a temperature in the range of from about 15° C. to about 100° C. and a hydrogen pressure in the range of from atmospheric pressure to about 100 bar.

16. The process of claim 15 wherein said process is conducted at a temperature in the range of from about 25° C. to about 70° C. and a pressure in the range of from about 5 to about 70 bar.

17. The process of claim 1 wherein said process is conducted in a polar medium.

18. The process of claim 17 wherein said polar medium is diethylene glycol dimethyl ether.

19. The process of claim 1 wherein the monoalkynically unsaturated diol and the monoalkenically unsaturated diol are diols of general formula

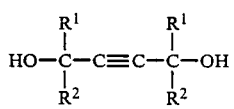

respectively of general formula

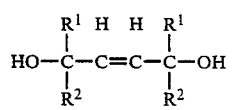

wherein each pair of $R^1$ and each pair of $R^2$ individually is H or $CH_3$.

20. The process of claim 19 wherein the alkynically unsaturated diol is but-2-yne-1,4-diol.

21. The process of claim 19 wherein the palladium compound is a cation-providing compound.

* * * * *